US006251670B1

(12) United States Patent
Yoshimoto et al.

(10) Patent No.: US 6,251,670 B1
(45) Date of Patent: Jun. 26, 2001

(54) METHOD OF CULTURING CELLS IN SUSPENSION USING LECTINS

(75) Inventors: Tanihiro Yoshimoto; Hiroyuki Takamatsu, both of Kanazawa (JP)

(73) Assignee: President of Kanazawa University, Kanazawa (JP)

(*) Notice: Subject to any disclaimer, the term of this patent is extended or adjusted under 35 U.S.C. 154(b) by 0 days.

(21) Appl. No.: 09/340,035

(22) Filed: Jun. 28, 1999

(30) Foreign Application Priority Data

Jun. 29, 1998 (JP) ................................. 10-182450

(51) Int. Cl.[7] .................................................. C12N 5/00

(52) U.S. Cl. ...................... 435/383; 435/346; 435/404; 435/325

(58) Field of Search ................................... 435/383, 404, 435/346, 325

(56) References Cited

U.S. PATENT DOCUMENTS 4,594,327 * 6/1986 Zuk .
4,695,553 * 9/1987 Wardlaw et al. .
5,693,760 * 12/1997 Seilhammer et al. ................ 530/396

FOREIGN PATENT DOCUMENTS 1-165374 * 6/1989 (JP) .

OTHER PUBLICATIONS

R. Baluna et al, (Abstract) "Fibronectin Inhibits the Cytotoxic Effect of Ricin A Chain on Endothelial Cells", Journal: Int. J. Immunopharmacol., vol. 18, Issue 6–7, pp. 355–361 (1996).

R. Baluna et al, (Abstract) "Evidence for a Structural Motif in Toxins and Interleukin-2 That May be Responsible for Binding to Endothelial Cells and Initiating Vascular Leak Symdrome" Journal: Proc. Natl. Acad. Sci. USA, vol. 96, Issue: 7, pp. 3957–3962 (1999).

M.G. Battelli et al, (Abstract) "Toxicity and Cytotoxicity of Nigrin B, A Two–Chain Ribosome–Inactivating Protein from Sambucus Nigra: Comparison With Ricin" Journal: Arch Toxicol, vol. 71, Issue: 6, pp. 360–364, (1997).

C.E. Bennett et al, (Abstract) "Studies on Toxicity and Binding Kenetics of Abrin in Normal and Epstein Barr Virus–Transformed Lymphocyte Culture–I: Experimental Results–2", Journal: Exp. Cell Biol., vol. 49, Issue: 6, pp. 319–326 (1981).

B. Bernard et al, (Abstract) "Changes in the Sensitivity of Chick Fibroblasts to Ricinus Lectin (RCA I) Toxicity in Relation to the Stage of Embryo Development" Journal: Biochem. J., vol. 182, Issue: 1, pp. 33–38 (1979).

R.F. Brown et al. (Abstract) "Ultrastructure of Rat Lung Following Inhalation of Ricin Aerosol" Journal: Int. J. Exp. Pathol., vol. 78, Issue: 4, pp. 267–276 (1997).

C. Campbell et al, (Abstract) "A Dominant Mutation to Ricin Resistance in Chinese Hamster Ovary Cells Induces UDP–GLcNAc: Glycopeptide Beta–4–N–Acetylglucosaminyltransferase III Activity" Journal: J. Biol. Chem., vol. 259, Issue: 21, pp. 13370–13378 (1984).

M.M. Campos et al (Abstract) "Effect of Canatoxin on Cell Cultures", Journal: Cell Biol. Int. Rep. vol. 15, Issue: 7, pp. 581–594 (1991).

M.R. Carvalho et al (Abstract) "Relative Importance of Phytohemagglutinin (Lectin) and Trypsinchymotrypsin Inhibitor on Bean (Phaseolus vulgaris L) Protein Absroption and Utilization by the Rat" Journal J. Nutr. Sci. Vitaminol (Tokyo), vol. 44, Issue: 5, pp. 685–696 (1998).

B. Chazaud et al, (Abstract) "Ricin Toxicity and Intracellular Routing in Tumoral HT–29 Cells. II. Differential Ricin Toxicity from the Apical and Basolateral Surfaces of Differentiated HT–29 Cells" Journal: Exp. Cell Res., vol. 221, Issue: 1, pp. 214–220 (1995).

L. Citores et al, (Abstract) "Differential Sensitivity of HeLa Cells to the Type 2 Ribosome–Inactivating Proteins Ebulin I, Nigrin B and Nigrin F as Compared with Ricin" Journal: Cell Mol. Biol (Noisy–Le–Grand), vol. 42, Issue: 4, pp. 473–476 (1996).

M. Derenzini et al, (Abstract) "Toxic Effects of Ricin: Studies on the Pathogenesis of Liver Lesions" Journal: Virchows Arch. B Cell Pathol., vol. 20, Issue: 1, pp. 15–28 (1976).

P.S. Distefano et al. (Abstract) "Selective Destruction of Nerve Growth Factor Receptor–Bearing Cells in Vitro Using a Hybrid Toxin Composed of Ricin A Chain and a Monoclonal Antibody Against the Nerve Growth Factor Receptor" Journal: J. Cell Biol., vol. 101, Issue: 3, pp. 1107–1114 (1985).

M. Dodeur et al, (Abstract) "Toxic Effect of Ricinus Lectin on Hepatoma Cells in Relation to Enzyme Modification of the Cell Surface", Journal: Biochim. Biophys. Acta., vol. 628, Issue: 3, pp. 303–313 (1980).

(List continued on next page.)

*Primary Examiner*—Leon B. Lankford, Jr.
(74) *Attorney, Agent, or Firm*—Oblon, Spivak, McClelland, Maier & Neustadt, P.C.

(57) ABSTRACT

An object of the present invention is to provide a method of enabling perfusion culture efficiently and simply by agglutinating cells with Lectin, which is a naturally-occurring agglutinin, thereby separating the cells and the culture medium. According to the method of the present invention, lectin is added to a culture medium to quickly agglutinate and precipitate the cells, thereby separating the culture medium and the cells. Hence, it is easy to remove old culture medium and replenish with fresh culture medium. Accordingly, if the method of the present invention is used, the perfusion culture is performed automatically and on an industrial scale.

8 Claims, 4 Drawing Sheets

(1 of 4 Drawing Sheet(s) Filed in Color)

OTHER PUBLICATIONS

R.J. Fulton et al, (Abstract) "Purification of Ricin A1, A2 and B Chains and Characterization of Their Toxicity", Journal: J. Biol. Chem., vol. 261, Issue: 12, pp. 5314–5319 (1986).

K. Ghoreschi et al, (Abstract) "Functional Role of CD95 Ligand in Concanavalin A–Induced Intestinal Intraepithelial Lymphocyte Cytotoxicity", Journal: Immunology, vol. 95, Issue: 4, pp. 566–571 (1998).

T. Griffin et al, (Abstract) "Selective Cytotoxicity of a Ricin A–Chain–Anti–Carcinoembryonic Antigen Antibody Conjugate for a Human Colon Adenocarcinoma Cell Line" Journal: J. Natl. Cancer Inst., vol. 69, Issue: 4, pp. 799–805 (1982).

T. Griffin et al, (Abstract) "In Vitro Cytotoxicity of Recombinant Ricin A Chain–Antitransferrin Receptor Immunotoxin Against Human Adenocarcinomas of the Colon and Pancreas", Journal: J. Biol. Response Mod., vol. 7, Issue: 6, pp. 559–567 (1988).

G.D. Griffiths et al, (Abstract) "Examination of the Toxicity of Several Protein Toxins of Plant Origin Using Bovine Pulmonary Endothelial Cells", Journal: Toxicology, vol. 90, Issue: 1–2, pp. 11–27 (1994).

A. Gupta et al, (Abstract) "Phytohemagglutinin Rapidly Lyses S49 T–Lymphoma Cells and the Cytotoxicity is Not Mediated by Generation of cAMP or Increase in Cytosolic Calcium", Journal: Biochem. Biophys Res. Commun., vol. 170, Issue: 3, pp. 1035–1043 (1990).

R. Hedge et al, (Abstract) "Purification and Characterization of Three Toxins and Two Agglutinins from Abrus Precatorius Seed by Using Lactamyl–Sepharose Affinity Chromatography", Journal: Anal. Biochem., vol. 194, Issue: 1, pp. 101–109 (1991).

J. Hoshino et al, (Abstract) "Sensitivity in Vitro of Mature and Immature Mouse Thymocytes to Dexamethasone Cytotoxicity and its Correlation to Poly ADP–Ribosylation", Journal: Biochem. Int., vol. 27, Issue: 1, pp. 105–116 (1992).

D. Hudson et al (Abstract) "Non–Specific Cytotoxicity of Wheat Gliadin Components Towards Cultured Human Cells", Journal: Lancet., vol. 1, Issue 7955, pp. 339–341 (1976).

R.C. Hughes et al, (Abstract) "Effect of 2–Deoxy–D–Glucose on the Cell–Surface Glycoproteins of Hamster Fibroblasts", Journal: Eur. J. Biochem., vol. 72, Issue: 2, pp. 265–272 (1977).

F.I. Ikegwuonu et al, (Abstract) "The Toxicity of Phytohemagglutinis to Chick Embryos", Journal: Toxicon, vol. 14, Issue: 2, pp. 139–141 (1976).

H. Imada et al, (Abstract) "Influence of PHA Stimulation on the Cytotoxicity and Mutagenicity of X–Rays and Ethylnitrosourea in Human Peripheral Blood T–Lymphocytes", Journal: Mutat Res., vol. 310, Issue: 1, pp. 55–64 (310).

D.E. Johnston et al, (Abstract) "Purification of Cultured Primary Rat Hepatocytes Using Selection with Ricin A Subunit", Journal: Hepatology, vol. 20, Issue: 2, pp. 436–444 (1994).

C. Jones, (Abstract) "Increased Cytotoxicity of Normal Rabbit Serum for Lectin–Resistant Mutants of Animal Cells", Journal: J. Exp. Med., vol. 160, Issue: 4, pp. 1241–1246 (1984).

M.J.Kik et al, (Abstract) "Pathological Effects of Phaseolus Vulgaris Isolectins on Pig Jejunal Mucosa in Organ Culture", Journal: Gut., Fol. 32, Issue: 8, pp. 886–892 (1991).

M. Koga et al (Abstract) "Cytotoxic, cell Agglutinating, and Syncytium Forming Effect of Purified Lectins from Ricinus Communis on Cultured Cells", Journal: Gann, vol. 70, Issue: 5, pp. 585–591 (1979).

J. Lafont et al, (Abstract) "Duodenal Toxicity of Dietary Phaseolus Vulgaris Lectins in the Rat: An Intergrative Assay", Journal: Digestion, vol. 41, Issue: 2, pp. 83–93 (1988).

D.C. Laux et al, (Abstract) "Lectin–Dependent Cell–Mediated Cytotoxicity: Assessment of Cytotoxic Reactivity Following Challenge with Syngeneic Tumors", Journal: J. Natl. Cancer Inst., vol. 72, Issue: 3, pp. 667–672 (1984).

M. Leist et al (Abstract) "A Novel Mechanism of Murine Hepatocyte Death Inducible by Concanavalin A", Journal: J. Hepatol, vol. 25, Issue: 6, pp. 948–959 (1996).

Y.J. Lidor et al (Abstract) "Alkylating Agents and Immunotoxins Exert Synergistic Cytotoxic Activity Against Ovarian Cancer Cells. Mechanism of Action", Journal: J. Clin. Invest., vol. 92, Issue: 5, pp. 2440–2447 (1993).

L.H. Lin et al, (Abstract) "Clones From Cultured, B16 Mourse–Melanoma Cells Resistant to Wheat–Germ Agglutinin and With Altered Production of Mucin–Type Gluycoproteins", Journal: Carbohydr. Res., vol. 111, Issue: 2, pp. 257–271 (1983).

G.M. Liuzzi et al (Abstract) "Regulation of Gelatinases in Microglia and Astrocyte Cell Cultures by Plant Lectins", Journal: Glia., vol. 27, Issue: 1, pp. 53–61 (1999).

P. Lorea et al. (Abstract) "In Tritro Characterization of Lectin–Induced Alternations on the Proliferative Activity of Three Human Melanoma Cells Lines", Journal: Melanoma Res., vol. 7, Issue: 5, pp. 353–363 (1997).

P. Luther et al (Abstract) "[Isolation and Characterization of Mistletoe Extracts (Viscum Album L.), II. Effect of Agglutinating and Cytotoxic Fractions on Mouse Ascites Tumor Cells]", Journal: Acta. Biol. Med. Ger., vol. 36, Issue: 1, pp. 119–125 (1977).

T.J. Lynch (Abstract) "Immunotoxin Therapy of Small–Cell Lung Cancer. N901–Blocked Ricin for Relapsed Small–Cell Lung Cancer", Journal: Chest, vol. 103, Issue: 4 Suppl., pp. 436S–439S (1993).

S. Madan et al (Abstract) "Enhancing Potency of Liposomal Monensin on Ricin Cytotoxicity in Mouse Macrophage Tumor Cells", Journal: Biochem. Int., vol. 28, Issue: 2 pp. 287–295 (1992).

S. Magnusson et al (Abstract) "Interactions of Ricin With Sinusoidal Endothelial Rat Liver Cells. Different Involvement of Two Distinct Carbohydrate–Specific Mechanisms in Surface Binding and Internalization", Journal: Biochem. J. vol. 277, Issue: Pt 3, pp. 855–861 (1991).

B. Mockel et al (Abstract) "Effects of Mistletoe Lectin I on Human Blood Cell Lines and Peripheral Blood Cells. Cytotoxicity, Apoptosis and Induction of Cytokines", Journal: Arzneimittelforschung, vol. 47, Issue: 10, pp. 1145–1151 (1997).

S.M. Naseem et al (Abstract) "The Role of Calcium Ions for the Expression of Ricin Toxicity in Cultured Macrophages", Journal: J. Biochem. Toxicol, vol. 7, Issue: 2, pp. 133–138 (1992).

A. Nogradi et al (Abstract) "The Use of a Neurotoxic Lectin Volkensin, to Induce Loss of Identified Motoneuron Pools", Journal: Neuroscience, vol. 50, Issue: 4, pp. 975–986 (1992).

T. Oda et al (Abstract) "Binding and Cytotoxicity of Ricinus Communis Lectins to HeLa Cells, Sarcoma 180 Ascites Tumor Cells and Erythrocytes", Journal: J. Biochem (Tokyo), vol. 96, Issue: 2, pp. 377–384 (1984).

P.D. Pinnaduwage et al (Abstract) "Characteristics of Two Wheat Germ Agglutinin–Resistant Variants of B16 Mouse Melanoma Cells with Reduced Tumorigenicity", Journal: Carbohydr. Res., vol. 151, pp. 37–50 (1986).

O.M. Pitts (Abstract) "Con A Cytotoxicity: A Model for the Study of Key Signaling Steps Leading to Lymphocyte Apotosis in Aids?", Journal: Med. Hypotheses, vol. 45, Issue: 3, pp. 311–315 (1995).

B. Ray et al (Abstract) "Enhancement of Cytotoxicities of Ricin and Pseudomonas Toxin in Chinese Hamster Ovary Cells by Nigericin", Journal: Mol. Cell Biol., vol. 1, Issue: 6, pp. 552–559 (1981).

J. Ripka et al (Abstract) "Novel Glycosylation–Defective Baby Hamster Kidney Cells", Journal: Biochem. Biophys Res. Commun., vol. 186, Issue: 1, pp. 102–113 (1992).

M. Sargiacomo et al (Abstract) "A Cytotoxic, Photolabile Cross–Linking Derivative of Ricin. Action on Various Cells and Application to the Study of Ricin Toxicity", Journal: Exp. Cell Res., vol. 142, Issue: 2, pp. 283–292 (1982).

R.E. Schwarz et al (Abstract) "Phytohemagglutinin–L (PHA–L) Lectin Surface Binding of N–Linked Beta 1–6 Carbohydrate and Its Relationship to Activated Mutant Ras in Human Pancreatic Cancer Cell Lines", Journal: Cancer Lett., vol. 107, Issue: 2, pp. 285–291 (1996).

R.E. Schwartz et al (Abstract) "Weatgerm Agglutinin–Mediated Toxicity in Pancreatic Cancer Cells", Journal: Br. J. Cancer, vol. 80, Issue: 11, pp. 1754–1762 (1999).

D.L. Simpson et al (Abstract) "Killing of Cultured Hepatocytes by Conjugates of Asialofetuin and EGF Linked to the A Chains of Ricin or Diphtheria Toxin", Journal: Cell, vol. 29, Issue: 2, pp. 469–473 (1982).

G.L. Soni et al "Intraperitoneal Toxicity of Pea and Lentil Lectins in Albino Rats—Efect on Growth and Osmotic Fragility of Erythrocytes", Journal: Indian J. Exp. Biol., Issue: 3, pp. 280–281 (1991).

P. Stanley et al (Abstract) "Complementation Between Mutants of Cho Cells Resistant to a Variaty of Plant Lectins", Journal: Somatic Cell Genet, vol. 3, Issue: 4, pp. 391–405 (1977).

F. Stirpe et al, (Abstract) "Properties of Volkensin, a Toxic Lectin from Adenia Volkensil", Journal: J. Biol. Chem., vol. 260, Issue: 27, pp. 14589–14595 (1985).

A.G. Tonevitskii et al (Abstract) "Selective Cytotoxic Effect of an Immunotoxin on Human Erythroid Tumor Cells", Journal: Mol. Biol. (Mosk), vol. 25, Issue: 5, pp. 1181–1187 (1991).

A.G. Tonevitsky et al (Abstract) "Hybridoma Cells Producing Antibodies Against A–Chain of Mistletoe Lectin I Are Resistant to This Toxin", Journal: Immunol. Lett., vol. 46, Issue: 1–2, pp. 5–8 (1995).

L.P. Vernon et al (Abstract) "A Toxic Thionin From Pyrularia Pubera: Purification, Properties, and Amino Acid Sequence", Journal: Arch Biochem. Biophys., vol. 238, Issue: 1, pp. 18–29 (1985).

E.S. Vitetta et al (Abstract) "Phase I Immunotoxin Trial in Patients With B–Cell Lymphoma", Journal: Cancer Res., vol. 51, Issue: 15, pp. 4052–4058 (1991).

A. Wiedlocha et al (Abstract) "Specific Killing of Mouse Leukemic Cells With Ricin A–Chain Immunotoxin", Journal: Arch. Immunol. Ther. Exp. (Warsz), vol. 37, Issue: 1–2, pp. 101–113 (1989).

T. Yamaguchi et al (Abstract) "Different Cytotoxicity of Ricin and a Concanavalin A–Ricin A Chain Conjugate Between Bald/3T3 Cells and the Transformed Cells", Journal: J. Pharmacobiodyn, vol. 5, Issue: 9, pp. 678–685 (1982).

T. Yoshida et al (Abstract) "Enhancement of the Cytotoxicity of Mistletoe Lectin–1 (ML–1) by High pH or Perturbation in Golgi Functions", Journal: Pharmazie, vol. 46, Issue: 5, pp. 349–351 (1991).

John G. Aunins, et al. "Induced Flocculation of Animal Cells in Suspension Culture", vol. 34, 1989, pp. 629–638.*

* cited by examiner

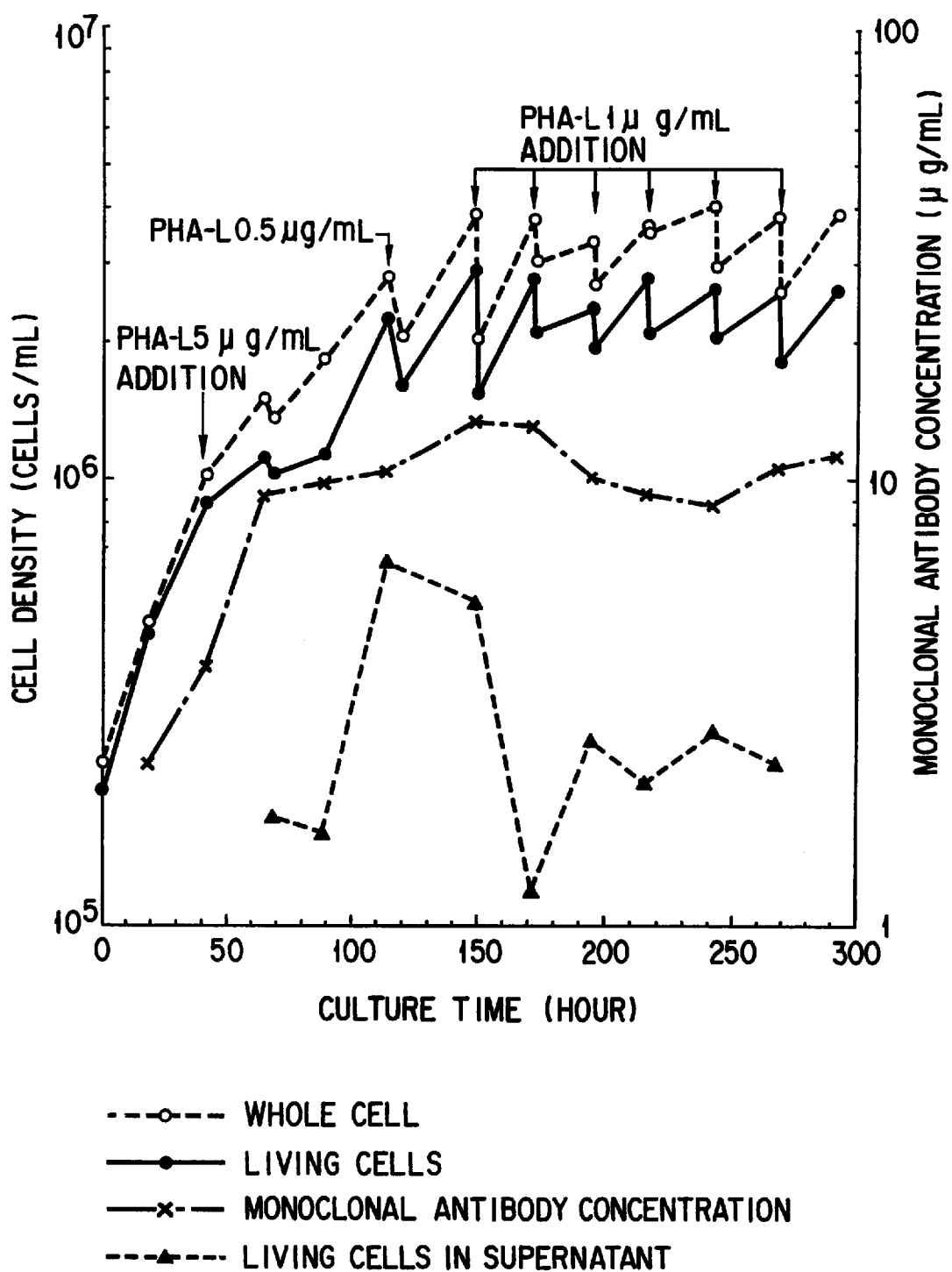
F I G. 1

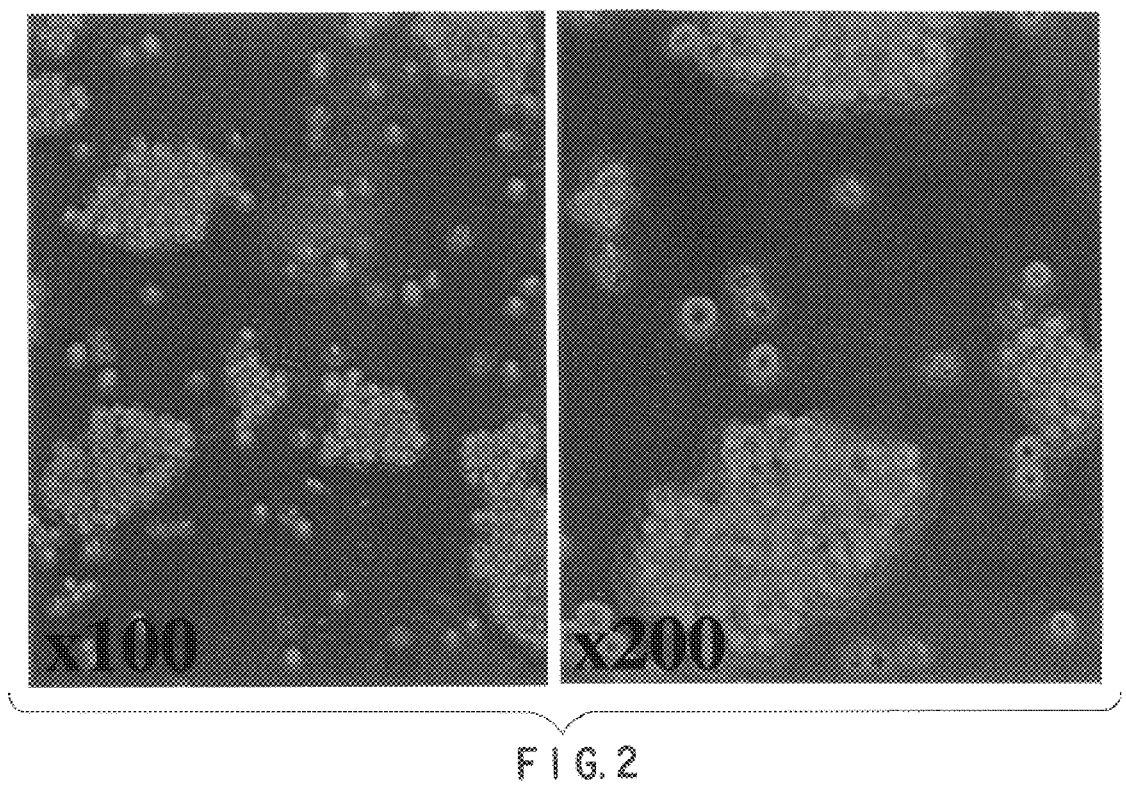
F I G. 2

METHOD OF CULTURING CELLS IN SUSPENSION USING LECTINS

BACKGROUND OF THE INVENTION

The present invention relates to a method of perfusion culture using a naturally-occurring agglutinin.

It has been strongly desired to develop a technique for producing useful bioactive substances such as hormones, cytokines, and monoclonal antibodies in a large amount by culturing a large amount of cells. In consideration of an industrial scale production, suspension culture, in which cells are proliferated while floating in a culture medium without attaching to a culture immobilization carrier, is considered as the most useful method since the production is easily scaled up.

However, in the cell culture, since growth inhibitors are excreted from the cells, cell proliferation will stop at a relatively low cell density unless the culture medium containing the growth inhibitor is removed. Hence, to culture cells in a large amount and with a high density, it is necessary to perform perfusion culture while old culture medium containing the growth inhibitors is appropriately discharged from a vessel and replaced with fresh culture medium.

To perform the perfusion culture, it is very important to precipitate living cells quickly in the culture medium in order to separate the living cells and the old culture medium, thereby discharging the old culture medium from a culture vessel.

Conventional methods to separate the culture medium and the living cells include (1) a method using a filter, (2) a method using gravity, (3) a method using a centrifuge, and (4) a method immobilizing cells to a carrier.

However, the method (1) has a problem in that filter clogging takes place. The method (2) has a problem in that separation efficiency is low since the specific gravity of animal cells is about 1.1. The method (3) has problems in that the apparatus has a complicated structure, and that the centrifugal force will have an adverse effect on the cells. The method (4) has drawbacks in that a troublesome operation is required for immobilization, and that it is difficult to scale up the production. As described, none of them is a satisfactory method for culturing a large amount of cells.

Furthermore, Japanese Patent Application KOKAI Publication No. 1-165374 discloses a method for improving separation efficiency of the cells from a culture medium by agglutinating the cells by addition of a mixture of polyacrylic acid and chitosan as an agglutinant, to the culture medium. All drawbacks associated with the aforementioned methods can be overcome by this method.

However, this method has the following disadvantages.

(i) Polyacrylic acid and chitosan, which are non-biological substances, may possibly cause cytotoxicity.

(ii) Relatively large amount of polyacrylic acid/chitosan (50–200 $\mu$g/mL) is needed to effectively agglutinate animal cells.

(iii) Chitosan produced from chitin by its heat treatment under strong alkali condition is not uniform from lot to lot. This non-uniformity is inappropriate for the process of producing medicine with respect to safety.

(iv) Agglutinate formed with polyacrylic acid/chitosan are too large (0.1 to 2.0 mm in diameter) for its core to be supplied with enough oxygen and nutrients.

BRIEF SUMMARY OF THE INVENTION

An object of the present invention is to provide a method of attaining perfusion culture efficiently and simply by agglutinating cells with lectin, which is a naturally occurring agglutinative substance, thereby separating the cells and culture medium.

To attain the aforementioned object, the present invention provides a method of culturing cells comprising the steps of:

(1) suspending cells in a culture medium before or after lectin is added to the culture medium, and culturing the cells;

(2) separating the cells agglutinated by an action of lectin in the culture medium from the culture medium and removing all or a portion of the culture medium;

(3) replenishing the cells with fresh culture medium, adding lectin to the culture medium at any timepoint, and culturing the cells; and (4) repeating operations set forth in the steps (2) and (3) for times arbitrarily set.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The file of this patent contains at least one photograph executed in color. Copies of this patent with color photograph will be provided by the Patent and Trademark Office upon request and payment of the necessary fee.

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a graph showing a yield of LOX-2 cells produced by continuous culture according to the culturing method of the present invention and a yield of monoclonal antibodies produced by the LOX-2 cells;

FIG. 2 shows microscopic photographs of agglutinates of LOX-2 cells produced by the culturing method of the present invention;

DETAILED DESCRIPTION OF THE INVENTION

Figure 3:
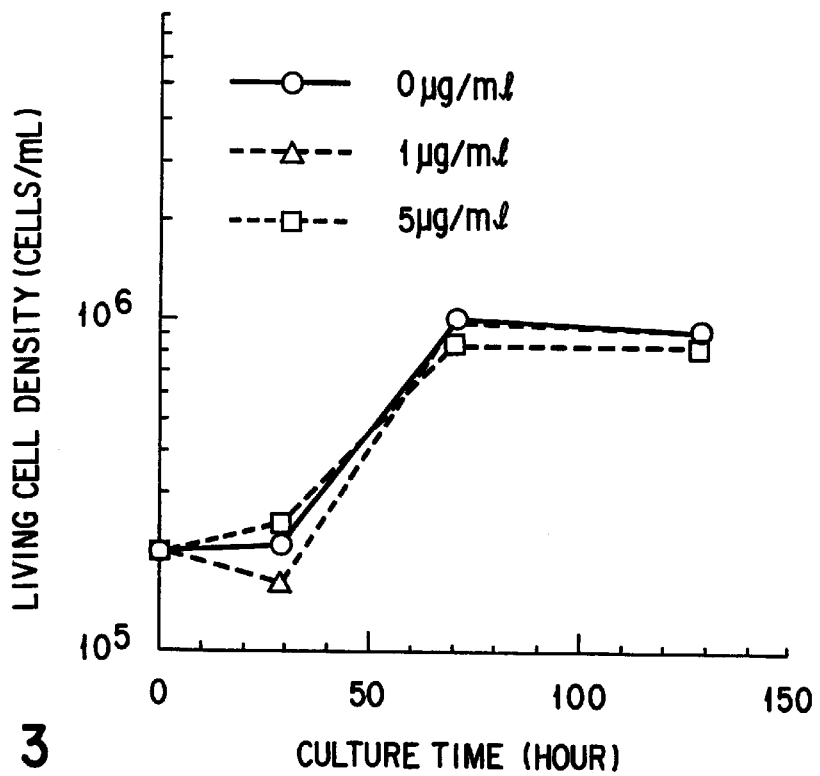
FIG. 3 is a time course of stationary culture of LOX-2 cells in the presence of PHA-L.

In the present invention, the culture medium and cells are efficiently separated from each other by adding lectin in the culture medium to agglutinate the cells.

The method of the present invention was accomplished on the basis of findings made by the present inventors that cells, such as hybridomas, producing a useful bioactive substance, are effectively agglutinated by lectin.

The "lectin" used in the present invention is a sugar binding protein found in animal, vegetable or bacterial cells, and characterized by (1) being a non-immunological product, (2) capable of agglutinating animal and vegetable cells, (3) precipitating a polysaccharide or a complex carbohydrate, (4) having bi-valence or more, and (5) capable of determining a binding specificity to a saccharide by an inhibition test using a monosaccharide or an oligosaccharide.

Examples of the lectin include Lectin from *Phaseolus vulgaris* (hereinafter, referred to as "PHA-L"), Lectin from Glycine max, and Lectin from Pokeweed mitogen. Besides these, Lectin from *Canavalia ensiformis* (Concanavalin A) is also included. However, lectin is not limited to these. All of the sugar binding proteins satisfying the aforementioned definition are included.

Lectin has a specificity to a sugar chain, so that the type of lectin to be used must be determined depending upon the type of the sugar present on the cell to be cultured. Since there are various types of lectins having different specificities to sugar chains and whose specificities have been clarified, it is easy to screen lectin suitable for use.

In the method of the present invention, lectin does not substantially exhibit cytotoxicity for a long time. Therefore, if the method of the present invention is used, cells can be cultured constantly in a culture medium containing lectin and the operation for adding lectin is no longer required in exchanging the culture medium. Hence, if the method of the present invention is used, it is extremely easy to industrialize and automatically perform the perfusion culture.

Any cell may be used in the method of the present invention as long as it can produce a useful bioactive substance and be agglutinated by the action of lectin.

The useful bioactive substances may be, but not limited to, proteinous or peptidergic substances such as cytokine, erythropoietin, protein C, various antibodies, hormones, enzymes, and receptors. All substances to be preferably harvested from the cells may be included.

Accordingly, the cells to be used in the method of the present invention include immunocytes such as lymphocytes and macrophages, hybridomas, and hormone producing cells such as renal cells and pancreatic cells.

The cells to be used in the method of the present invention may be recombinant cells into which a gene encoding any of the aforementioned useful bioactive substances is introduced by a genetic engineering method.

Furthermore, since the lectin to be used in the method of the present invention is a protein, it is possible to use the recombinant cell into which a gene encoding a protein portion of the lectin is introduced by a genetic engineering method. If such a recombinant cell is used, it is not necessary to add lectin to the culture medium. Therefore, such an embodiment would be quite advantageous in view of cost. Since the sequence of a lectin gene and a method of introducing the sequence into cells are well known, it is possible for a person skilled in the art to produce the recombinant cells without difficulty.

It is also possible to further introduce a gene encoding any of the aforementioned useful bioactive substances into the cells in which the gene encoding the protein portion of a lectin has been introduced by the genetic engineering method.

The method of the present invention is further applicable to culturing tissues and organs. In the method of the present invention, any culture medium may be used as long as it is suitable for culturing cells and does not substantially inhibit agglutination of the cells by lectin. Such a culture medium may be, but not limited to, a generally used Dulbecco's modified Eagle's medium and HAT medium.

Furthermore, if necessary, any additive may be added to the culture medium as long as it does not substantially inhibit agglutination of the cells by lectin.

According to the method of the present invention, it is possible to separate the cells and the culture medium from each other by any method known to those skilled in the art. Examples of such a method may include a method for naturally precipitating the cells agglutinated by lectin and a method using a filter. However, the natural sedimentation method is more preferable since this method is operated simply and does not give any physical stimulus to the cells. In the case of using a filter, it is preferable to employ a filter having an aperture of 50 μm or less since the agglutinates of cells by lectin have sizes within about 100 to 150 μm. A commercially available filter is applicable.

After the cells and the culture medium are separated from each other, all or a portion of the culture medium is removed and then an appropriate amount of fresh culture medium, preferably the same amount of the fresh culture medium as the removed old medium, is replenished.

The method of the present invention is preferably applied to perfusion culture.

The apparatus to be used in the perfusion culture is known to those skilled in the art. The apparatus generally has an inlet port for introducing the culture medium and an outlet port for discharging the culture medium, and further comprises a suction pump and a discharge pump. In addition, inlet and outlet ports for gas are arranged in the apparatus for controlling a gas concentration (especially carbon dioxide concentration). It is preferable that a stirring wing be arranged in order to maintain a homogeneous composition of the culture medium by stirring it.

The apparatus is not limited in size as long as it is suitable for a desired scale of culture. Since the structure of the apparatus is simple, it may be obvious for those skilled in the art to enlarge the culturing scale.

[Embodiments]

Hereinbelow, examples of the present invention will be explained in detail.

[Example 1]

A spinner flask of 41 mm radius and 140 mm height, having a whole volume of 500 mL was used in this example. The flask had a stirring wing within it. The culture volume of the flask was 200 mL. 10% fetal bovine serum was added to Dulbecco's modified Eagle's medium and the resultant medium was used as a culture medium. PHA-L was added to the culture medium in an amount of 0.5, 1 or 5 μg/mL.

Hereinbelow, the culturing method and the results will be explained with reference to FIG. 1.

A culture medium sterilized by filtration was placed in a culture vessel of 200 mL which was previously sterilized in an autoclave. Subsequently, a mouse-mouse hybridoma LOX-2 strain, which was obtained by hybridizing a mouse myeloma SP2 with a mouse B cell, was inoculated in an amount of $2 \times 10^5$ cells/mL. The hybridomas produce IgG (anti 12 lipoxygenase antibody).

The culture vessel was placed in an incubator of 37° C. filled with carbon dioxide containing air. The culture vessel was equipped with a stirring wing. The stirring speed was set at 90 rpm. To prevent a pH increase of the culture medium, culturing was initiated in an atmosphere containing 7% carbon dioxide immediately after the inoculation.

Eighteen hours after culturing, the atmosphere was switched to an atmosphere containing 5% carbon dioxide and culturing was continued. When a living-cell density reached $9\times10^5$ cells/mL (41 hours of culturing), PHA-L was added to make a final concentration of 5 μg/mL. Immediately after the addition and later on, it was confirmed from outside the culture vessel that agglutinates were formed. Thereafter, sampling was performed over time. When the agglutinates were microscopically observed, the sizes became almost constant in about 22 hours. Microscopic images of the agglutinates at this time point are shown in FIG. 2. According to this, the diameters of the agglutinates fall within the range of about 100 to 150 μm (since the diameter of a cell is about 15 μm, a single agglutinate presumably contains several hundreds of cells).

23 hours after PHA-L was added, stirring was stopped for 30 minutes to exchange the culture medium, thereby precipitating the agglutinates. 100 mL of the supernatant was taken out from the culture vessel and then fresh culture medium containing no PHA-L was supplied to the culture vessel in an amount of 100 mL. The density of cells in the supernatant thus taken out was about $1.5\times10^5$ cells/mL. An additional exchange of the culture medium was similarly performed 88 hours after initiation of the culturing. In this case, no change was observed in cell density of the supernatant.

Thereafter, 100 mL of the supernatant was taken out 113 hours after initiation of the culture, in the same manner as above. The cell density of the supernatant significantly increased and the cell agglutinates reduced in size as shown in FIG. 1. Then, 100 mL of culture medium containing PHA-L in an amount of 1 μg/mL was added to the remaining culture medium (100 mL) in the culture vessel.

After 148 hours of the initiation of the culture, the culture medium was exchanged appropriately as shown in FIG. 1. At the time of exchanging the culture medium, 100 mL of the culture medium containing 2 μg/mL of PHA-L was added to the remaining culture medium (100 mL) in the culture vessel. The exchange of the culture medium was performed at intervals of 24 hours until the culture experiment was completed after 290 hours. Every time the culture medium was exchanged, the re-agglutination and the reduction in the density of cells in the supernatant removed out of the culture vessel were confirmed. More specifically, if the concentration of PHA-L in the culture medium was maintained at 1 μg/mL or more during the culture time, agglutinates were formed having diameters within about 50–150 μm (they are presumably formed of several tens–several hundreds of cells). The formed agglutinates were easily precipitated by a separation operation using natural gravitational sedimentation. An average density of living cells in the supernatant was $2.0\times10^5$ cells/mL (dotted line connecting solid triangles) as shown in FIG. 1, which was within 9.3% of the living cell density of the culture medium (solid line connecting solid circles in FIG. 1). When a concentration of the monoclonal antibodies was determined by the ELISA method, they were maintained at a concentration of about 10 μg/mL (dotted line connecting cross marks in FIG. 1).

According to the present invention, it was demonstrated that it is possible to culture the hybridoma LOX-2 cells while the cells are agglutinated by PHA-L, and that antibody productivity is maintained while the cells are cultured in the state of the agglutinates.

[Example 2]

Effects of PHA-L on cell proliferation and antibody productivity were further investigated by subjecting the hybridoma LOX-2 cells ($2\times10^5$ cells/ml) used in Example 1 to stationary culture performed in a culture flask containing 0.1 or 5 μg/mL of PHA-L. The results are shown in FIG. 3 and Table 1.

FIG. 3 shows that the living-cell density does not differ at any PHA-L concentration during the culturing period. It is therefore clear that PHA-L never show cytotoxity for a long time.

Table 1 shows the relationship between the LOX-2 agglutination ability and the PHA-L concentration and effects of PHA-L on the antibody productivity of LOX-2. From Table 1, it is demonstrated that LOX-2 shows a remarkable agglutination ability if PHA-L is added in an amount of 1 μg/mL or more, and that the antibody productivity of LOX-2 is never affected even if PHA-L is used in an amount of 5 μg/mL at most.

[Example 3]

In this embodiment, to study whether or not the method of the present invention was widely used for various purposes, myeloma SP-2, which was often used for producing hybridomas, was subjected to stationary culture to examine proliferation of the SP-2 cells. The SP-2 cells were inoculated in an amount of $1\times10^5$ cells/mL in a culture medium containing PHA-L in an amount of 0 or 1 μg/mL to determine a change of the living cells in density over time (FIG. 4) and the dependency (table 1) of the SP-2 agglutination ability upon the PHA-L concentration.

Figure 4:
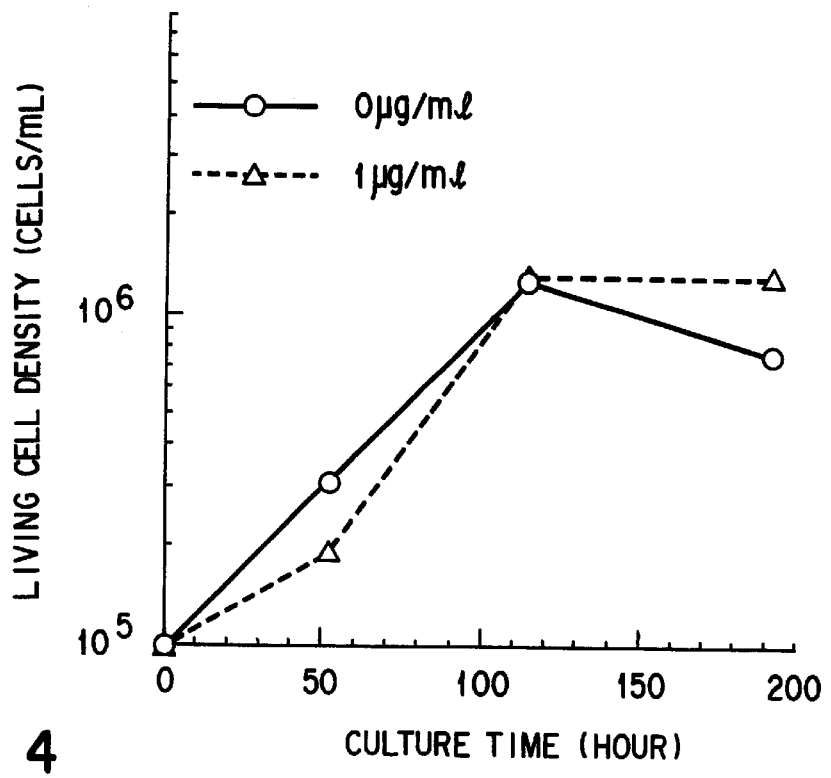
FIG. 4 is a time course of stationary culture of SP-2 cells in the presence of PHA-L.

FIG. 4 shows that the density of the living cells does not change at all if PHA-L is added in an amount of up to 1 μg/mL. FIG. 1 shows that the SP-2 cells are agglutinated effectively by PHA-L of 1 μg/mL or more.

According to this example, it was demonstrated that the method of the present invention is applicable to various cells.

[Example 4]

To determine a minimum concentration of PHA-L sufficient to induce agglutination of cells, culture mediums containing PHA-L in an amount of 0, 0.1, 0.5 and 1 μg/mL, were prepared. LOX-2 cells were inoculated in an amount of $2\times10^5$ cells/mL and subjected to stationary culture. The agglutination of the LOX-2 cells was microscopically observed.

As shown in Table 1, no agglutination was observed in the cultures containing 0 and 0.1 μg/mL of PHA-L. The agglutination observed in the culture containing 0.5 μg/mL of PHA-L was weak.

From the foregoing, it is found that the concentration of PHA-L must be 1 μg/mL in order to form the agglutination of the LOX-2 cells.

[Example 5]

Figure 5:
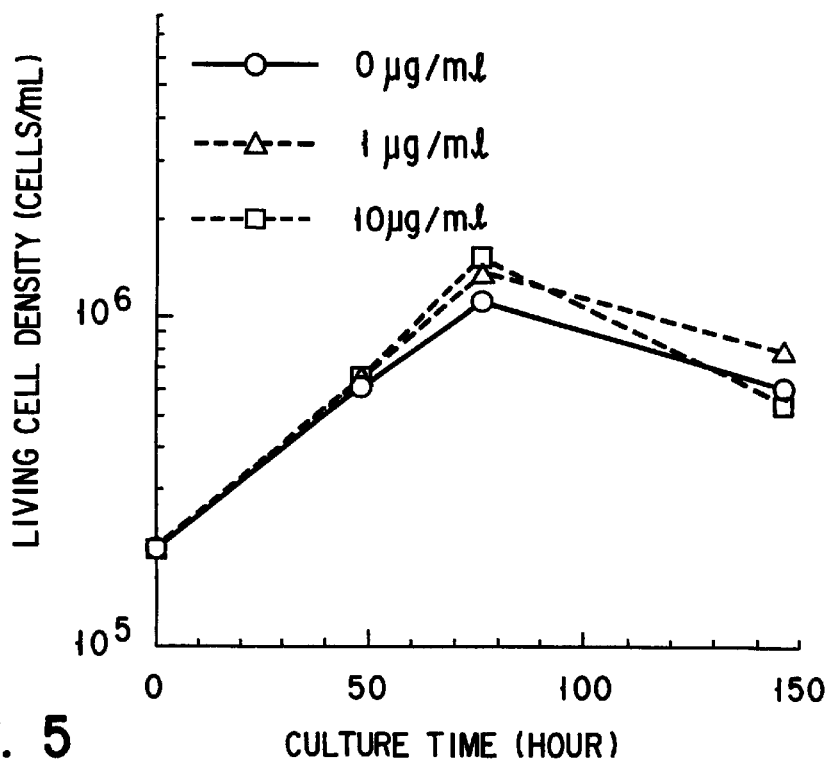
FIG. 5 is a time course of stationary culture of LOX-2 cells in the presence of soybean lectin (Lectin from Glycine max)

In this example, Lectin from Glycine max was used in place of PHA-L in order to check whether or not the LOX-2 cells were agglutinated with another type of lectin. Concentrations of Lectin from Glycine max used herein were 0.1 and 10 μg/mL. The LOX-2 cells were inoculated in an amount of $2\times10^5$ cells/mL to check the agglutination ability (Table 2) and the cell proliferation (FIG. 5). From Table 2, it is apparent that Lectin from Glycine max is also capable of agglutinating the cells. From FIG. 5, it is found that the proliferation of the cells over time is not affected by Lectin from Glycine max.

[Example 6]

In this example, it was demonstrated that the sugar chain recognized by lectin and present on a cell surface, had a specific structure, and that agglutination were are not formed unless lectin corresponding to the sugar chain structure present on the cell was added.

Figure 6:
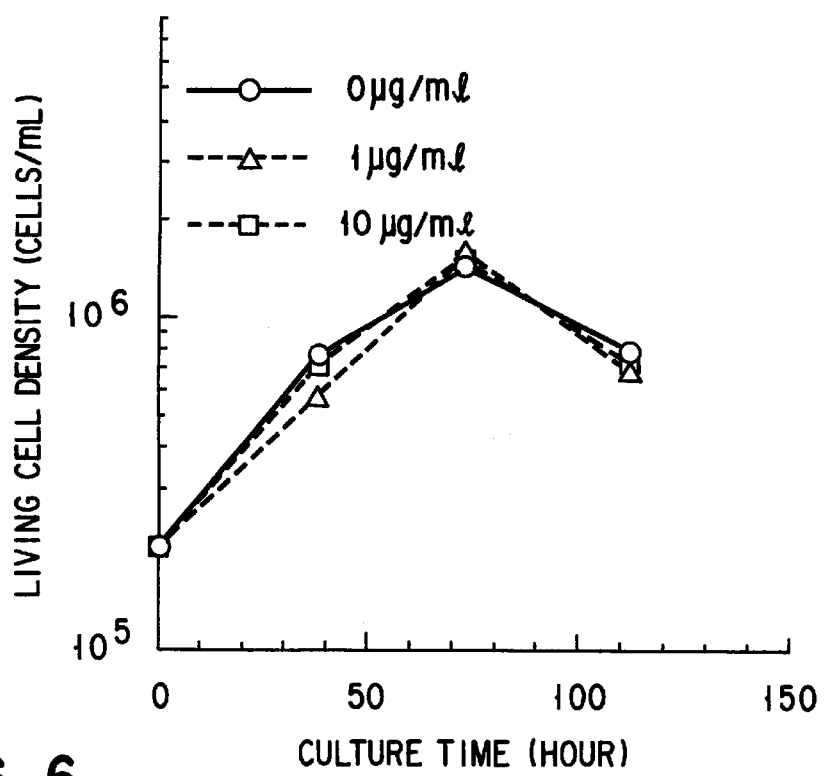
FIG. 6 is a time course of stationary culture of LOX-2 cells in the presence of Lectin from Pokeweed mitogen.

Lectin used in this example was Lectin from Pokeweed mitogen (PWM). The LOX-2 cells were inoculated in mediums containing 0, 1, and 10 µg/mL of PWM to check the agglutination ability of the cells (Table 3) and cell proliferation (FIG. 6). From FIG. 6, it is found that PWM has no effect upon the cell proliferation. As is apparent from Table 3, the LOX-2 cells were not agglutinated even when PWM was used in an amount of 10 µg/mL at most.

From the foregoing, it is clear that lectin has a specificity in recognizing the sugar chain. Therefore, it is demonstrated that it is necessary to select an appropriate lectin in accordance with a type of a sugar chain present on a surface of the cell to be used.

TABLE 1

| PHA-L concentration (µg/ml) | LOX-2 Agglutination State | LOX-2 antibody productivity (µg/mL)[1] | SP-2 agglutination ability |
| --- | --- | --- | --- |
| 0 | − | 11.0 | − |
| 0.1 | − | Not measured | Not measured |
| 0.5 | + | Not measured | Not measured |
| 1 | ++ | 9.4 | ++ |
| 5 | +++ | 10.8 | +++ |

Note: [1]values measured 128 hours after initiation of culture in FIG. 3.
Agglutination ability
−: Agglutination is not observed
+: Agglutinates of about 20–50 µm diameter are formed
++: Agglutinates of about 50–100 µm diameter are formed
+++: Aggregation masses of about 100-150 µm diameter are formed

TABLE 2

| Lectin from Glycine max concentration (µg/mL) | LOX-2 agglutination state | LOX-2 antibody productivity (µg/mL)[1] |
| --- | --- | --- |
| 0 | − | 18.2 |
| 1 | + | 16.6 |
| 10 | ++ | 15.4 |

Note: [1]Values measured 76 hours after initiation of culture in FIG. 5.
Agglutination ability
−: Agglutination is not observed
+: Agglutinates of about 20–50 µm diameter are formed
++: Agglutinates of about 50-100 µm diameter are formed
+++: Agglutinates of about 100-150 µm diameter are formed

TABLE 3

| PWM Concentration (µg/mL) | LOX-2 agglutination state | LOX-2 antibody Productivity (µg/mL)[1] |
| --- | --- | --- |
| 0 | − | 14.9 |
| 1 | − | 14.6 |
| 10 | − | 24.0 |

Note: [1]Values measured 112 hours after initiation of culture in FIG. 6.
Agglutination state
−: Agglutination is not observed
+: Agglutinates of about 20-50 µm diameter are formed
++: Agglutinates of about 50-100 µm diameter are formed
+++: Agglutinates of about 100-150 µm diameter are formed In the suspension culture method of the present invention, lectin is added to a culture medium to quickly precipitate cells, thereby separating the cells from the culture medium. It is therefore easy to remove old culture medium and replenish with new culture medium. Since lectin used in the present invention is a naturally occurring substance, it does not show substantial cytotoxicity, unlike an artificial agglutinative substance conventionally used. In addition, low concentration of lectin (1 µg/mL) is able to agglutinate animal cells effectively, and the agguluutinates thus formed are small enough (50–100 µm in diameter) to be replenished with oxygen and nutrients. The method of the present invention does not require the complicated operation and appliances as conventionally used. Therefore, if the method of the present invention is used, it is possible to perform perfusion culture automatically and on an industrial scale. Consequently, useful bioactive substances such as monoclonal antibodies and cytokines, can be produced at low cost and in a large amount.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of culturing cells, comprising:

(1) suspension culturing cells in a medium;

(2) adding a lectin to the medium to agglutinate the cells, thereby phase-separating the agglutinated cells from the medium;

(3) recovering the agglutinated cells from said medium;

(4) adding fresh medium to the agglutinated recovered cells, thereby suspending the cells in the medium; and (5) repeating (1)–(4).

2. The method according to claim 1, wherein in (2) the cells are separated from the medium by natural gravitation.

3. The method according to claim 1, wherein the cells are animal cells.

4. The method according to claim 1, wherein the cells are bybridomas.

5. A method of culturing cells, comprising:

(1) suspension culturing cells in a medium, wherein the cells are prepared by transfection of a gene encoding a protein portion of a lectin, and the cells produce the lectin in the medium;

(2) aggregating the cells with a lectin produced by the cells and recovering the aggregated cells;

(3) adding fresh medium to the cells recovered, thereby suspending the recovered cells in the ; and (4) repeating (1)–(3).

6. The method according to claim 5, wherein in (2) the cells are separated from the medium by natural gravitation.

7. The method according to claim 5, wherein the cells are animal cells.

8. The method according to claim 5, wherein the cells are hybridomas.

* * * * *